(12) United States Patent
Boyle

(10) Patent No.: US 7,256,290 B1
(45) Date of Patent: Aug. 14, 2007

(54) TITANIUM ALKOXIDE COMPOUND

(75) Inventor: Timothy J. Boyle, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 0 days.

(21) Appl. No.: 11/619,698

(22) Filed: Jan. 4, 2007

(51) Int. Cl.
*C07F 7/28* (2006.01)
(52) U.S. Cl. .............................. 546/6; 556/56
(58) Field of Classification Search ............ 556/56; 546/6

See application file for complete search history.

(56) References Cited

OTHER PUBLICATIONS

Boyle et al., Inorganic Chemistry, vol. 46, No. 5, pp. 1825-1835 (published on the Web Jan. 5, 2007).*

* cited by examiner

*Primary Examiner*—Porfirio Nazario-Gonzalez
(74) *Attorney, Agent, or Firm*—Elmer A. Klavetter

(57) ABSTRACT

A titanium alkoxide composition is provided, as represented by the chemical formula $(OC_6H_5N)_2Ti(OC_6H_5NH_2)_2$. As prepared, the compound is a crystalline substance with a hexavalent titanium atom bonded to two $OC_6H_5NH_2$ groups and two $OC_6H_5N$ groups with a theoretical molecular weight of 480.38, comprising 60.01% C, 5.04% H and 11.66% N.

9 Claims, 4 Drawing Sheets

TITANIUM ALKOXIDE COMPOUND

This invention was made with Government support under Contract No. DE-AC04-94AL85000 awarded by the Department of Energy. The Government has certain rights in the invention.

BACKGROUND OF THE INVENTION

The present invention relates generally to metal alkoxide compounds and more particularly to a titanium alkoxide compound of the formula $(OC_6H_5N)_2Ti(OC_6H_5NH_2)_2$.

Metal alkoxides $(M(OR)_x)$ are excellent precursors for the preparation of ceramic oxide materials and have applications ranging from electro-active ceramics, conductors, semiconductors, and catalysts. The structural arrangement of the precursor has been shown to play a significant role in determining the properties of the final materials. Unfortunately, controlling the structure of even the simplest $M(OR)_x$ species has not been realized; therefore, predicting the final structure of complex, mixed-ligand $M(OR)_x$ species is not yet possible. The variable noted for $M(OR)_x$ species is often attributed to the small charge to large cation radius ratio that requires the metal to bind additional ligands (i.e., bridging) to complete their coordination sphere. This phenomenon leads to uncontrolled cluster formation. In addition, the ligands often decompose to form oxides and unexpected structural rearrangements are often reported for supposed simple modification to $M(OR)_x$.

In order to minimize the oligomerization behavior of $M(OR)_x$, a number of bulky ligands have been introduced to fill coordination sites without depleting the charge of the metal. Of these, the monodentate tert-butyloxide is considered one of the more sterically demanding ligands available and is often used to limit oligomerization although oligomers still predominate compared with produced monomeric species. One alkoxide ligand that has been successfully used to reduce clustering was tetrahydrofurfuryl alcohol (H-OTHF). The bidentate H-OTHF ligand is constructed in such a manner that it will preferentially chelate due to the non-charged Lewis bind site of the heterocycle THF. Other ligands that have been used include the thiophene methanol (H-OTPM) and pyridine methanol or 2-pyridylcarbinol (H—OPy) ligands.

DETAILED DESCRIPTION OF THE INVENTION

Figure 1:
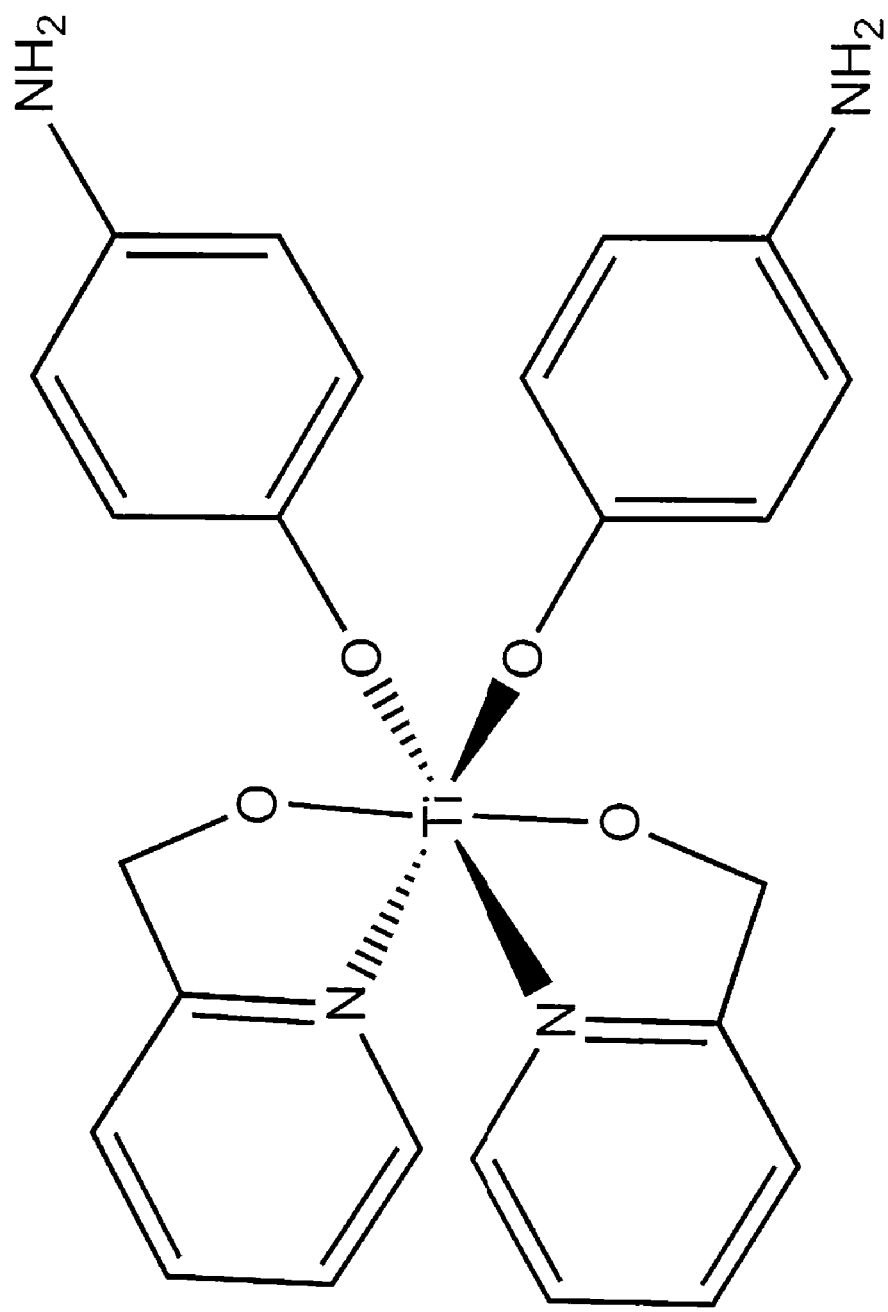
FIG. 1 illustrates the structure of $(OC_6H_5N)_2Ti(OC_6H_5NH_2)_2$.

The present invention relates to a specific metal alkoxide composition and structure, represented by the chemical formula $(OC_6H_5N)_2Ti(OC_6H_5NH_2)_2$, as depicted in FIG. 1. As prepared, the compound is a crystalline substance with a hexavalent titanium atom bonded to two $OC_6H_5NH_2$ groups and two $OC_6H_5N$ groups with a theoretical molecular weight of 480.38, comprising 60.01% C, 5.04% H and 11.66% N. Experimentally derived values of prepared $(OC_6H_5N)_2Ti(OC_6H_5NH_2)_2$ as determined by elemental analysis found 60.65% C, 5.08% H, 11.74% N.

In the preparation process of the $(OC_6H_5N)_2Ti(OC_6H_5NH_2)_2$ compound of the present invention, a Lewis base solvent is added to aid in solubilizing the titanium alkoxide compound. The solubilized mixture can be heated to remove the solvent, producing the crystalline $(OC_6H_5N)_2Ti(OC_6H_5NH_2)_2$ compound or, in another embodiment, the solvent can be allowed to remain in the resulting crystalline structure as a solvent adduct. In this latter embodiment, the resulting material is referred to as $(OC_6H_5N)_2Ti(OC_6H_5NH_2)_2 \cdot (solvent)$, indicating that the solvent remains in the crystalline structure with the titanium alkoxide compound of the present invention.

Figure 2:
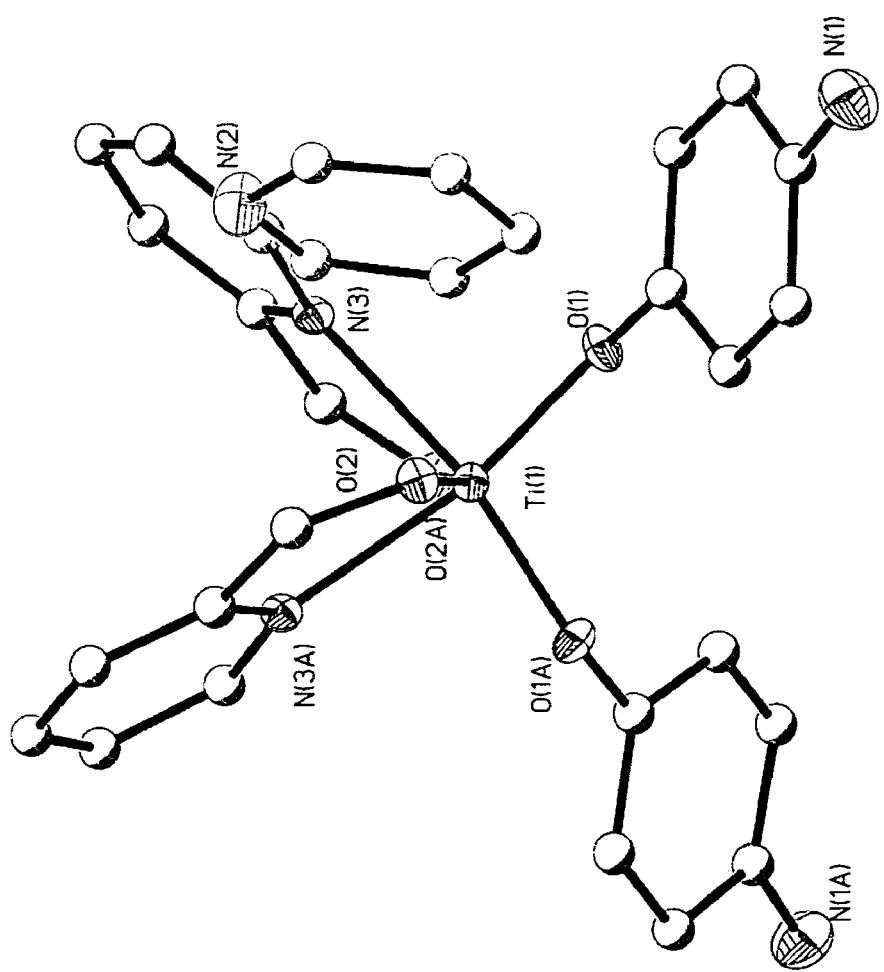
FIG. 2 illustrates the structure of $(OC_6H_5N)_2Ti(OC_6H_5NH_2)_2 \cdot C_5H_5N$.
Figure 3:
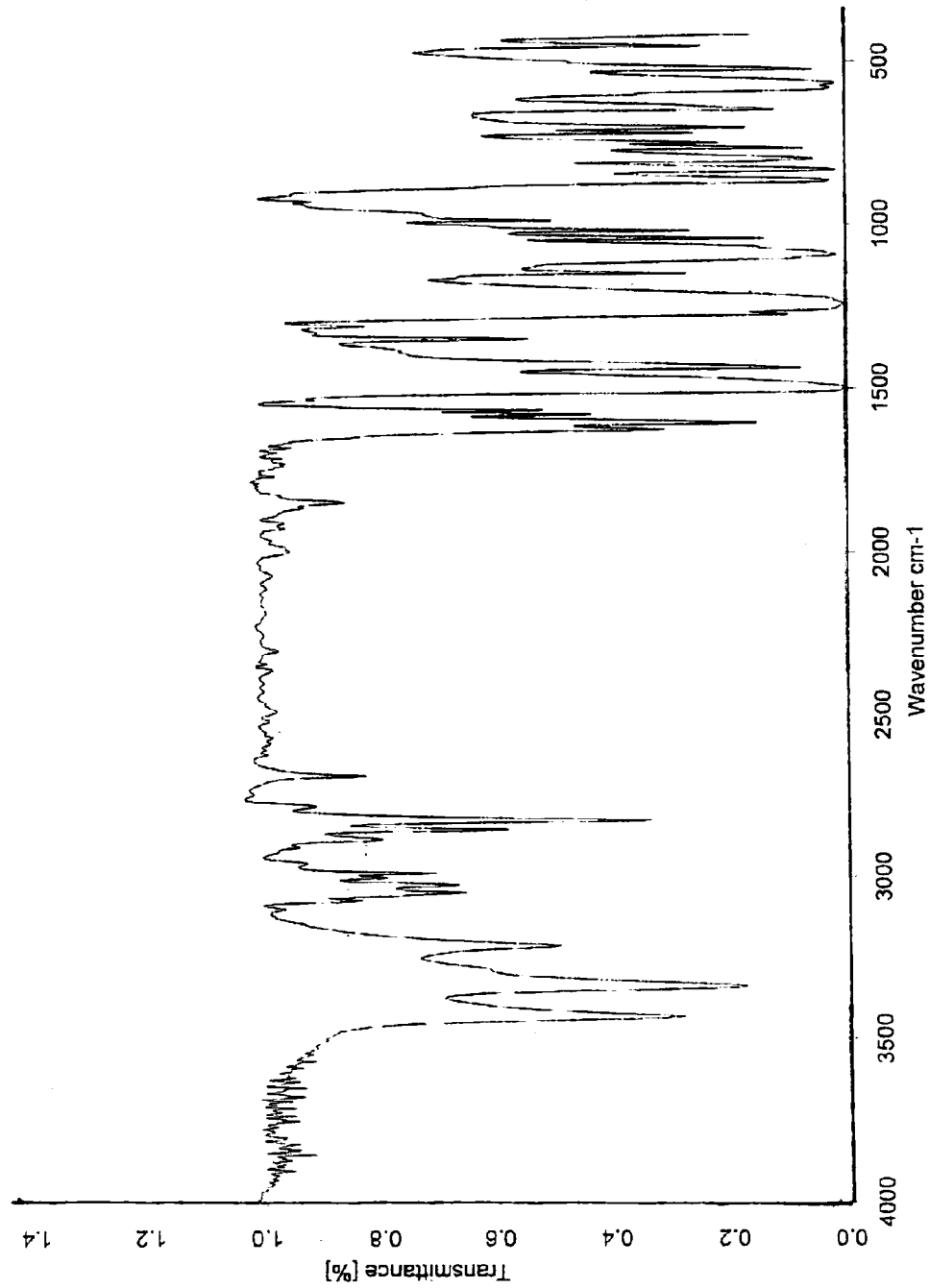
FIG. 3 shows Fourier Transform Infrared spectroscopy data for $(OC_6H_5N)_2Ti(OC_6H_5NH_2)_2 \cdot C_5H_5N$.
Figure 4:
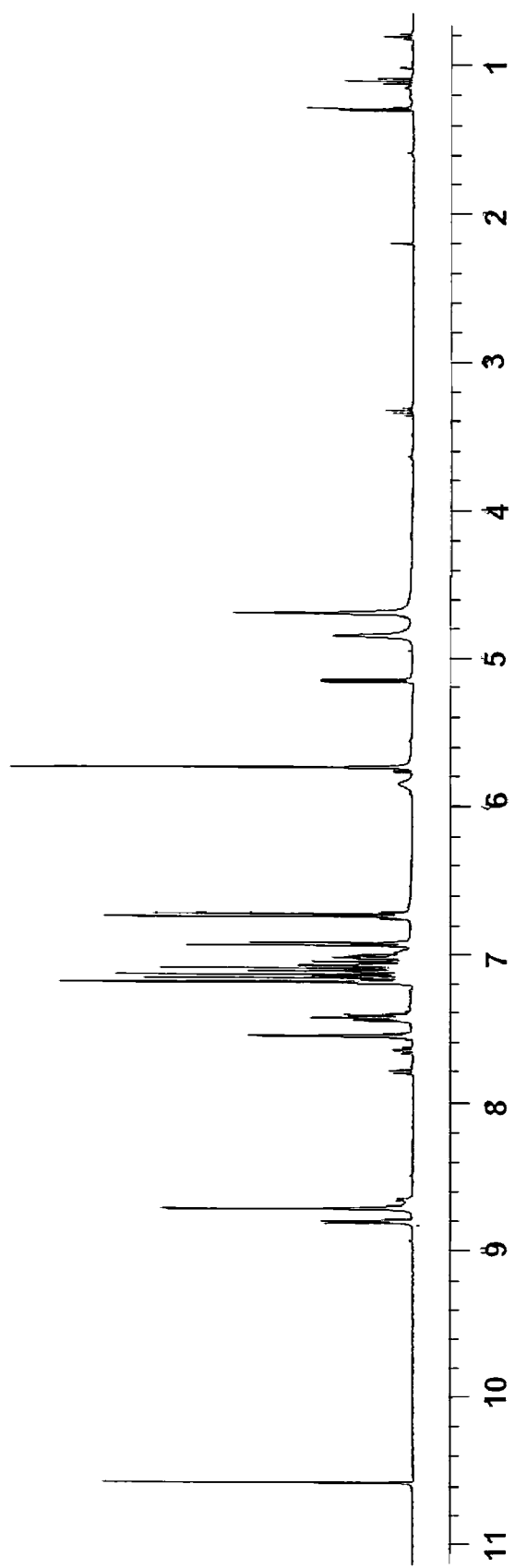
FIG. 4 shows nuclear magnetic resonance spectroscopy data for $(OC_6H_5N)_2Ti(OC_6H_5NH_2)_2 \cdot C_5H_5N$.

The Lewis base solvent used in the preparation is generally an amine-based solvent and can include, but is not limited to, amine-based solvents that can solubilize $(OC_6H_5N)_2Ti(OC_6H_5NH_2)_2$, such as nitrogen-based aromatic heterocyclic compounds as pyridine and substituted pyridine compounds and aniline and substituted aniline compounds, as well as amine-based alkyl compounds, including alkyl amines and substituted alkyl amines. In one preparation in which pyridine was used as the solvent, a pyridine adduct was present in the resulting crystalline structure comprising the compound of the present invention as a product of the preparation process. In one embodiment, the pyridine adduct was removed through heating to leave the $(OC_6H_5N)_2Ti(OC_6H_5NH_2)_2$ compound; in another embodiment, the pyridine was allowed to remain in the crystalline structure. A depiction of the $(OC_6H_5N)_2Ti(OC_6H_5NH_2)_2$ compound with the pyridine adduct is shown in FIG. 2.

To determine crystal structure information, a crystal sample of the prepared materials was mounted onto a thin glass fiber and placed under a liquid $N_2$ vapor stream onto a diffractometer. The radiation used was graphite monochromatized Mo K$\alpha$ radiation ($\lambda$=0.7107 Å). The lattice parameters were optimized from a least-squares calculation on carefully centered reflections. Lattice determination and data collection were carried out using SMART Version 5.054 software. Data reduction was performed using SAINTPLUS Version 6.01 software. The structure refinement was performed using XSHELL 3.0 software. The data were corrected for absorption using the SADABS program within the SAINT software package. All analysis software use algorithms standard in the art.

The structure was solved using direct methods. This procedure yielded the heavy atoms, along with a number of the C atoms. Subsequent Fourier synthesis yielded the remaining C atom positions. The hydrogen atoms were fixed in positions of ideal geometry and refined within the XSHELL software. These idealized hydrogen atoms had their isotropic temperature factors fixed at 1.2 or 1.5 times the equivalent isotropic U of the C atoms for which they were bonded. The final refinement of each compound included anisotropic thermal parameters on all non-hydrogen atoms. Table 1 shows the crystal data and structure refinement for the crystalline material formed that has the $C_{24}H_{24}N_4O_4Ti$ material with the $C_5H_5N$ adduct present. The crystal structure determined was checked using CI/PLATON full publication check at the International Union of Crystallography web site and database; there was no compound reported with the crystalline structure determined for the crystalline material of the present invention.

TABLE 1

| Crystal data and structure refinement for $C_{24}H_{24}N_4O_4Ti \cdot C_5H_5N$ | |
|---|---|
| Empirical formula | $C_{24}H_{24}N_4O_4Ti \cdot C_5H_5N$ |
| Formula weight | 559.47 |
| Temp (K) | 273(2) |
| Crystal system, space group | Ortho-rhombic Pccn |
| Unit cell dimensions | a = 12.5716(18) Å |
| | b = 12.8307(19) Å |
| | c = 16.406(2) Å |
| Volume (Å$^3$) | 2646.3(7) |
| Z | 1 |
| Calculated density | 1.404 Mg/m$^3$ |
| Absorption coefficient μ (Mo, Kα) | 0.369 mm$^{-1}$ |
| R1 (%) (all data) | 7.50 (12.07) |
| wR2 (%) (all data) | 12.44 (13.74) |

TABLE 2

| Metrical data for $C_{24}H_{24}N_4O_4Ti \cdot C_5H_5N$ | |
|---|---|
| Av. Ti-N$_{OPy}$ (Å) | 2.24 |
| Av. Ti-O$_{OPy}$ (Å) | 1.87 |
| Av. Ti-OR (Å) | |
| Selected angles around Ti (deg). | |
| O(1)-Ti(1)-O(1) | 101.79(18) |
| O(1)-Ti(1)-N(3) | 88.67(12) |
| Color | red-orange |
| UV-vis (cm$^{-1}$) (in toluene) | 281, 313(b), 384(b) |

The invention being thus described, it will be apparent to those skilled in the art that the same may be varied. Such variations are not to be regarded as a departure from the spirit and scope of the invention, and all such modifications are intended to be included within the scope of the following claims.

I claim:

1. A compound of the formula

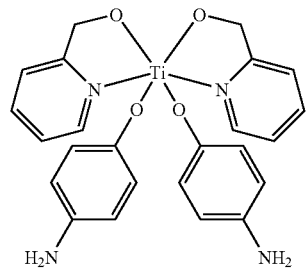

2. The compound of claim 1 having a theoretical molecular weight of 480.38, comprising 60.01% C, 5.04% H and 11.66% N.

3. A crystalline compound comprising $(OC_6H_5N)_2Ti(OC_6H_5NH_2)_2$. (solvent), wherein (solvent) is a solvent adduct in the crystalline compound.

4. The crystalline compound of claim 3 wherein said solvent adduct is a Lewis base capable of supporting the solubilization of $(OC_6H_5N)_2Ti(OC_6H_5NH_2)_2$.

5. The crystalline compound of claim 4 wherein said solvent adduct results from an amine-based solvent.

6. The crystalline compound of claim 5 wherein said amine-based solvent is selected from the group consisting of pyridine, substituted pyridine compounds, aniline, substituted aniline compounds, alkyl amines and substituted alkyl amines.

7. The crystalline compound of claim 5 wherein said amine-based solvent is pyridine and the crystalline compound comprises $(OC_6H_5N)_2Ti(OC_6H_5NH_2)_2 \cdot (C_5H_5N)$.

8. The crystalline compound of claim 7 wherein said crystalline compound has a molecular weight of 559.5.

9. The crystalline compound of claim 7 wherein the crystalline compound has an ortho-rhombic structure with unit cell dimensions of a=12.5716 Å, b=12.8307 Å and c=16.406 Å.

* * * * *